_United States Patent_ [19]

Barker et al.

[11] Patent Number: 4,847,386

[45] Date of Patent: Jul. 11, 1989

[54] PROCESS FOR PREPARING THIOPHENE DERIVATIVES

[75] Inventors: John M. Barker, Ruddington; Patrick R. Huddleston, Chilwell, both of England

[73] Assignee: Shell Internationale Research Maatschappij B.V., The Hague, Netherlands

[21] Appl. No.: 212,334

[22] Filed: Jun. 27, 1988

[30] Foreign Application Priority Data

Jul. 7, 1987 [GB] United Kingdom ................. 8715924
May 11, 1988 [GB] United Kingdom ................. 8811177

[51] Int. Cl.$^4$ .................. C07D 333/36; C07D 333/38
[52] U.S. Cl. ......................................... 549/68; 549/61
[58] Field of Search .................................. 549/61, 68

[56] References Cited

U.S. PATENT DOCUMENTS

| | | | |
|---|---|---|---|
| 2,443,598 | 6/1948 | Cheney et al. | 549/68 |
| 2,502,423 | 4/1950 | Cheney et al. | 549/68 |
| 3,445,473 | 5/1969 | Ruschig et al. | 549/68 |
| 4,317,915 | 3/1982 | Confalone et al. | 549/68 |
| 4,428,963 | 1/1984 | Confalone et al. | 514/447 |

OTHER PUBLICATIONS

Baker, B. R., et al., J. Org. Chem., 18, 138–152, (1953).

_Primary Examiner_—Alan Siegel

[57] ABSTRACT

A process for the preparation of 3-aminothiophenes or acid-addition salts thereof, which comprises reacting the corresponding 3-oxotetrahydrothiophenes with an acid-addition salt of hydroxylamine in the presence of a polar inert solvent and in the absence of a base at a temperature in the range of from 0° to 200° C.

12 Claims, No Drawings

PROCESS FOR PREPARING THIOPHENE DERIVATIVES

The present invention relates to a process for the preparation of 3-aminothiophenes.

Baker et. al. J. Org. Chem., 18,138,(1953) describe a two step process for the preparation of 3-amino-4-methoxycarbonylthiophene hydrochloride from 3-oxo-4-methoxycarbonyltetrahydrothiophene. The process comprises reacting 3-oxo-4-methoxycarbonyltetrahydrothiophene with hydroxylamine (formed in situ from hydroxylamine hydrochloride and barium carbonate) in the presence of methanol, isolating 3-oximino-4-methoxycarbonyltetrahydrothiophene, and reacting this isolated oxime with hydrogen chloride in the presence of ether and methanol. Both steps in the process require long reaction times.

Surprisingly it has now been found that 3-aminothiophenes may advantageously be prepared from the corresponding 3-oxotetrahydrothiophenes in a single step process.

Accordingly the present invention provides a process for the preparation of a 3-aminothiophene or an acid-addition salt thereof, which comprises reacting the corresponding 3-oxotetrahydrothiophene with an acid-addition salt of hydroxylamine in the presence of a polar inert solvent and in the absence of a base at a temperature in the range of from 0° to 200° C.

According to one preferred aspect of the invention, the 3-oxotetrahydrothiophene has a 4-alkoxycarbonyl substituent, and the reaction is effected at a temperature in the range of from 50° to 200° C.

According to another preferred aspect, the 3-oxotetrahydrothiophene is a compound of general formula

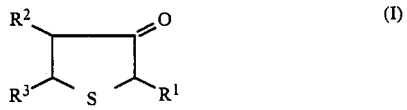

in which each of $R^1$, $R^2$ and $R^3$ is independently selected from hydrogen atoms and $COR^4$, cyano, nitro alkyl, aryl, and alkaryl groups, each $R^4$ being independently selected from alkoxy, hydroxy, alkyl, amino, alkylamino and dialkylamino groups.

When the 3-oxotetrahydrothiophene is a compound of general formula (I), preferably each of $R^1$, $R^2$ and $R^3$ is independently selected from hydrogen atoms and alkoxycarbonyl, cyano, alkyl and aryl groups. At least one of the substituents $R^1$, $R^2$ and $R^3$ is preferably selected from hydrogen atoms and alkoxycarbonyl groups. More preferably one of $R^1$, $R^2$ and $R^3$ is selected from a hydrogen atom and an alkoxycarbonyl group, another of $R^1$, $R^2$ and $R^3$ is selected from a hydrogen atom, an alkoxycarbonyl group and an alkyl group, and the remainder of $R^1$, $R^2$ and $R^3$ is selected from a hydrogen atom and an alkoxycarbonyl, cyano, alkyl and aryl group.

Alternatively, when the 3-oxotetrahydrothiophene is a compound of general formula (I), preferably one or more of $R^1$, $R^2$ and $R^3$ is or are independently selected from $COR^4$, cyano and nitro groups and the remainder is or are independently selected from hydrogen atoms and alkyl, aryl, and alkaryl groups, each $R^4$ being independently selected from alkoxy, hydroxy, alkyl, amino, alkylamino and dialkylamino groups. Preferably one or two of $R^1$, $R^2$ and $R^3$ is or are independently selected from alkoxycarbonyl, aminocarbonyl, alkylaminocarbonyl, dialkylaminocarbonyl, cyano and nitro groups and the remainder is or are independently selected from hydrogen atoms, alkyl groups and aryl groups. More preferably either one of $R^1$, $R^2$ and $R^3$ is a cyano group and the remainder are independently selected from hydrogen atoms, alkyl groups and aryl groups, or one or two of $R^1$, $R^2$ and $R^3$ is or are selected from alkoxycarbonyl groups and the remainder is or are independently selected from hydrogen atoms, alkyl groups and aryl groups.

Unless otherwise stated where reference is made to an alkyl group, it preferably means an alkyl group having from 1 to 6 carbon atoms, for example a methyl group. Where reference is made to an aryl group, it preferably means a phenyl group.

In the process according to the invention, the polar inert solvent is conveniently selected from nitriles, e.g. acetonitrile and propanonitrile; amides, e.g. N,N-dimethylformamide and N,N-dimethylacetamide; alkanols having up to 6 carbon atoms, e.g., methanol; and sulphoxides, e.g. dimethylsulphoxide. Preferably the solvent is acetonitrile.

Preferably the acid addition salt of hydroxylamine is a hydrogen halide salt, for example the hydrogen chloride salt, or hydroxylamine sulphate.

The reaction is preferably effected at a temperature in the range of from 50, more preferably 75° to 160° C., conveniently under reflux.

3-Oxotetrahydrothiophenes may be prepared according to known techniques, for example as described in "Thiophenes and its Derivatives, Volume 1" by S. Gronowitz (John Wiley and Sons, 1985), pages 152 to 153 and references cited therein.

3-Aminothiophenes are useful as intermediates in the preparation of pharmaceutical and/or agrochemical compounds. For example German patent application No. DE 3,305,866 describes the use of 3-amino-4-methoxycarbonylthiophene hydrochloride in the preparation of herbicidally active compounds, and European patent application publication number EPA 126970 describes the use of 3-amino-4-methoxycarbonylthiophene in the preparation of pharmaceutically active compounds. U.S. Pat. No. 4,428,963 also discloses the use of certain 3-aminothiophenes in the preparation of thiophene derivatives which are useful as blood lipid lowering agents and as antiobesity agents.

The following examples illustrate the invention.

EXAMPLE 1

4-Amino-3-methoxycarbonylthiophene hydrochloride

4-Oxo-3-methoxycarbonyltetrahydrothiophene (3.9 g) was heated under reflux for 1 hour with hydroxylamine hydrochloride (2 g) in acetonitrile 10 ml). The mixture was then cooled and the solid portion was filtered off and washed with dry diethyl ether to afford the title compound (3.65 g), m.p. 203°-204° C.

The yield of the title compound was 77%, which compares with a yield of 55% for the time-consuming two-step process reported in Baker et . al. J. Org. Chem., 18,138,(1953).

EXAMPLE 2

Preparation of 3-Amino-4,5-bismethoxycarbonylthiophene hydrochloride

3-Oxo-4,5-bismethoxycarbonyltetrahydrothiophene (2.65 g) was dissolved in propionitrile (5 ml) and hydroxylamine hydrochloride (1 g) was added. The mixture was heated under reflux on the steam bath for 1½ hours by which time it was almost solid. Ether was added to the cooled mixture and the title compound was filtered off. Yield 2.37 g (77.5%) M.P.166°–169° dec. 3-Amino-4,5-bismethoxycarbonylthiophene was liberated from the title compound by treatment with aqueous ammonia followed by bulk distillation (220° C., 0.1 mm Hg) and exhibited $^1$H n.m.r. $\delta$ (CDCl$_3$) 6.40 (1H,s), 4.40 (2H, brs), 3.90, 3.94 (2×3H,s).

EXAMPLE 3

Preparation of methyl 3-aminothiophene-2-carboxylate

2-Methoxycarbonyl-3-oxotetrahydrothiophene (2 g) was dissolved in acetonitrile (20 ml) with heating and stirring. Hydroxylamine hydrochloride (0.8 g) was added to the refluxing solution and the mixture was refluxed for 1½hour. After cooling, ether (50 ml) was added and the precipitated straw-coloured solid was filtered off. The solid was dissolved in water and basified with 4M ammonia solution and extracted with dichloromethane (2×25 ml). The combined extracts were washed with water and with brine and dried over sodium sulphate. Filtration and evaporation gave an oil which solidified on cooling and was crystallised from petrol ether bp 60°–80° to afford the title compound, 1.34 g (73%); mp 62°–63°.

EXAMPLE 4

Preparation of methyl 3-amino-4-methylthiophene-2-carboxylate

2-Methoxycarbonyl-4-methyl-3-oxotetrahydrothiophene (1.74 g) was dissolved in acetonitrile (13 ml) and the resulting solution was brought to the boil. To this was added hydroxylamine hydrochloride (0.69 g) and the mixture was refluxed for 5 hours. The reaction mixture was cooled in ice and dry ether (50 ml) added whereby a sticky precipitate was produced which was filtered off with the aid of kieselguhr. The kieselguhr was slurried with water and filtered, and the filtrate was basified with ammonia and extracted with ether (2 ×). The combined extracts were dried over sodium sulphate, filtered and evaporated to give the title compound, 1.1g (64%) mp 82°–83°.

EXAMPLE 5

Preparation of 3-amino-4-cyanothiophene hydrochloride

4-Cyano-3-oxotetrahydrothiophene (1.27 g) was dissolved in acetonitrile (15 ml) with heating and stirring. Hydroxylamine hydrochloride (0.69 g) was added to the refluxing solution and the mixture was refluxed for 1½hour. After cooling, ether (25 ml) was added and the title compound was filtered off and air-dried. Yield 1.35 g (84%); mp 244°–246°. $\delta'$H nmr (CDCl$_3$/DMSO-d$_6$) 9.2(br s) 8.55 (d, J=4Hz) 7.85 (d, J=4Hz).

EXAMPLES 6 to 10

By a method similar to that described in Example 1 the following 3-aminothiophenes were prepared.

TABLE 1

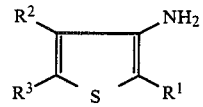

| Example | R$^1$ | R$^2$ | R$^3$ | Salt/Free base | Reaction Time (hr) | Percentage yield | n.m.r.$\delta$ (CDCl$_3$) (free base/ |
|---|---|---|---|---|---|---|---|
| 6 | CH$_3$ | CH$_3$O$_2$C | H | HCl | 1 | 52 | 7.8 (s, ThH); 4.5(br s, NH$_2$), 3.75(s, CH$_3$O$_2$C); 2.15 (s, ThCH$_3$) |
| 7 | H | CH$_3$O$_2$C | CH$_3$ | HCl | 1 | 59 | 5.7(2, ThH); 4.8 (br s, NH$_2$); 3.8(s, CH$_3$O$_2$C); 2.55(s, ThCH$_3$) |
| 8 | CH$_3$ | CH$_3$O$_2$C | CH$_3$ | HCl | 4 | 84 | 4.4(br s, NH$_2$); 3.9(s, CH$_3$O$_2$C); 2.6(s, Th—2-CH$_3$); 2.15(s, Th—5-CH$_3$) |
| 9 | H | CH$_3$O$_2$C | Phenyl | Free Base | 6 | 17 | 7.35(s, Ph); 6.15(s, ThH); 4.8(br s, NH$_2$); 3.6(s, CH$_3$O$_2$C) |
| 10 | H | H | CH$_3$O$_2$C | HCl | 1 | 82 | 7.35(d, J=1.8Hz, Th—3-H) 6.45(d, J=1.8Hz, Th—5-H 3.85(s, CH$_3$O$_2$C) ca 3.8 (br s, NH$_2$) |

EXAMPLE 11

3-Amino-4-methoxycarbonylthiophene hydrochloride

3-Oxo-4-methoxycarbonyltetrahydrothiophene (28 g) was heated under reflux for 1 hour with hydroxylamine hydrochloride (11.5 g) in methanol (80 ml). The mixture was then cooled and a first crop was filtered off and washed with dry diethyl ether to afford the title compound (18.4 g, 57.6%) m.p. 203° to 205° C. On further cooling a second crop (2.7 g, 8.5%) was obtained, m.p. 201° to 202° C. The total yield was thus 66.1%.

EXAMPLE 12

3-Aminothiophene

Hydroxylamine hydrochloride (1 g) was dissolved in methanol (9 ml) and 3-oxotetrahydrothiophene (1 g) added. After 16 hours at 20° C. the dark brown mixture was poured into diethylether (25 ml). The ether layer was extracted with water (40×10 ml), filtered through kieselguhr and the red solution was made basic with concentrated aqueous ammonia and extracted with methylene chloride. The extract was dried (sodium sulphate) and evaporated to give 0.52 g of a black oil, consisting of 3-aminothiophene (53% yield). 'H n.m.r. (CDCl$_3$) $\delta$6.1(dd), $\delta$6.6 (dd) $\delta$7.05 (dd).

We claim:

1. A process for the preparation of a 3-aminothiophene or an acid-addition salt thereof, which comprises reacting the corresponding 3-oxotetrahydrothiophene with an acid-addition salt of hydroxylamine in the presence of a polar inert solvent and in the absence of a base at a temperature in the range of from 0° to 200° C.

2. A process as claimed in claim 1, in which the 3-oxotetrahydrothiophene is a compound of general formula

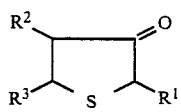

in which each of $R^1$, $R^2$ and $R^3$ is independently selected from hydrogen atoms and COR$^4$, cyano, nitro, alkyl, aryl, and alkaryl groups, each $R^4$ being independently selected from alkoxy, hydroxy, alkyl, amino, alkylamino and dialkylamino groups.

3. A process as claimed in claim 2, in which each of $R^1$, $R^2$ and $R^3$ is independently selected from hydrogen atoms and alkoxycarbonyl, cyano, alkyl and aryl groups.

4. A process as claimed in claim 3, in which at least one of $R^1$, $R^2$ and $R^3$ is selected from hydrogen atoms and alkoxycarbonyl groups.

5. A process as claimed in claim 4, in which one of $R^1$, $R^2$ and $R^3$ is selected from a hydrogen atom and an alkoxycarbonyl group, another of $R^1$, $R^2$ and $R^3$ is selected from a hydrogen atom, an alkoxycarbonyl group and an alkyl group, and the remainder of $R^1$, $R^2$ and $R^3$ is selected from a hydrogen atom and an alkoxycarbonyl, cyano, alkyl and aryl group.

6. A process as claimed in claim 2, in which one or more of $R^1$, $R^2$ and $R^3$ is or are independently selected from COR$^4$, cyano and nitro groups and the remainder is or are independently selected from hydrogen atoms and alkyl, aryl, and alkaryl groups, each $R^4$ being independently selected from alkoxy, hydroxy, alkyl, amino, alkylamino and dialkylamino groups.

7. A process as claimed in claim 6, in which one or two of $R^1$, $R^2$ and $R^3$ is or are independently selected from alkoxycarbonyl, aminocarbonyl, alkylaminocarbonyl, dialkylaminocarbonyl, cyano and nitro groups and the remainder is or are independently selected from hydrogen atoms, alkyl groups and aryl groups.

8. A process as claimed in claim 7, in which either one of $R^1$, $R^2$ and $R^3$ is a cyano group and the remainder are independently selected from hydrogen atoms, alkyl groups and aryl groups, or one or two of $R^1$, $R^2$ and $R^3$ is or are selected from alkoxycarbonyl groups and the remainder is or are independently selected from hydrogen atoms, alkyl groups and aryl groups.

9. A process as claimed in claim 1, in which the 3-oxotetrahydrothiophene has a 4-alkoxycarbonyl substituent, and the reaction is effected at a temperature in the range of from 50° to 200° C.

10. A process as claimed in any one of claims 1 to 9, in which the acid-addition salt of hydroxylamine is the hydrochloride.

11. A process as claimed in claim 1, in which the polar inert solvent is acetonitrile.

12. A process as claimed in claim 1, in which the reaction is effected at a temperature in the range of from 50° to 160° C.

* * * * *